US00PP30162P2

(12) United States Plant Patent
Bean

(10) Patent No.: US PP30,162 P2
(45) Date of Patent: Jan. 29, 2019

(54) ***AGAPANTHUS* PLANT NAMED 'MDB001'**

(50) Latin Name: ***Agapanthus* hybrid**
Varietal Denomination: MDB001

(71) Applicant: Charles Andrew de Wet, Johannesburg (ZA)

(72) Inventor: Quinton Bean, Johannesburg (ZA)

(73) Assignee: Charles Andrew Dewet, Johannesburg (ZA)

( * ) Notice: Subject to any disclaimer, the term of this patent is extended or adjusted under 35 U.S.C. 154(b) by 0 days.

(21) Appl. No.: 15/732,574

(22) Filed: Nov. 29, 2017

(51) Int. Cl.
*A01H 5/02* (2018.01)

(52) U.S. Cl.
USPC ..... Plt./398

(58) Field of Classification Search
USPC ..... Plt./398
See application file for complete search history.

*Primary Examiner* — Annette H Para
(74) *Attorney, Agent, or Firm* — Penny J. Aguirre

(57) ABSTRACT

A new cultivar of *Agapanthus*, 'MDB001', that is characterized by its white and blue bi-color flowers that are pendulous, its flower umbels that are large in size, and its compact plant habit with short and broad leaves.

2 Drawing Sheets

Botanical classification: *Agapanthus* hybrid.
Varietal denomination: 'MDB001'.

BACKGROUND OF THE INVENTION

The present invention relates to a new and distinct cultivar of *Agapanthus* of hybrid origin and will be referred to hereafter by its cultivar name, 'MDB001'. 'MDB001' represents a new perennial grown for landscape use.

The new cultivar was derived from a controlled breeding program by the Inventor in Hartebeespoort, Northwest Province, South Africa. The objective of the breeding program was to develop a new cultivar of *Agapanthus* of medium stature with neat foliage and bi-color flowers. The Inventor made a cross in November of 2008 between unnamed proprietary plants of *Agapanthus* from the Inventor's breeding program as both the female parent and male parent. The Inventor selected 'MDB001' in November of 2010 as a single unique plant amongst the seedlings that resulted from the above cross.

Asexual propagation of the new cultivar was first accomplished by division by the Inventor in Hartebeespoort, Northwest Province, South Africa in January of 2012. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'MDB001' as a distinct cultivar of *Agapanthus*.

1. 'MDB001' exhibits white and blue bi-color flowers that are pendulous.
2. 'MDB001' exhibits flower umbels that are large in size.
3. 'MDB001' exhibits a compact plant habit with short and broad leaves.

The female parent of 'MDB001' differs from 'MDB001' in having flowers that are held upright and leaves that are longer and strappy in appearance. The male parent of 'MDB001' differs from 'MDB001' in having flowers that are solid pale blue in color. 'MDB001' can be most closely compared to the *Agapanthus* cultivars 'AMBIC001' (U.S. Plant Pat. No. 25,519) and 'PMN06' (U.S. Plant Pat. No. 24,651). 'AMBIC001' and 'PMN06' are both similar to 'MDB001' in having bi-color flowers. 'AMBIC001' differs from 'MDB001' in having longer and thinner leaves and umbels that are smaller in size with shorter pedicels. 'PMN06' differs from 'MDB001' in having a larger plant size and lower inflorescence production.

BRIEF DESCRIPTION OF THE DRAWINGS

The accompanying colored photographs illustrate the overall appearance and distinct characteristics of the new *Agapanthus*. The photographs were taken of plants about 2 years in age (from a bare root division) of 'MDB001' as grown outdoors in a 3-gallon container in Hartebeespoort, Northwest Province, South Africa.

The photograph in FIG. 1 provides a side view of a plant of 'MDB001' in bloom.

Figure 1:
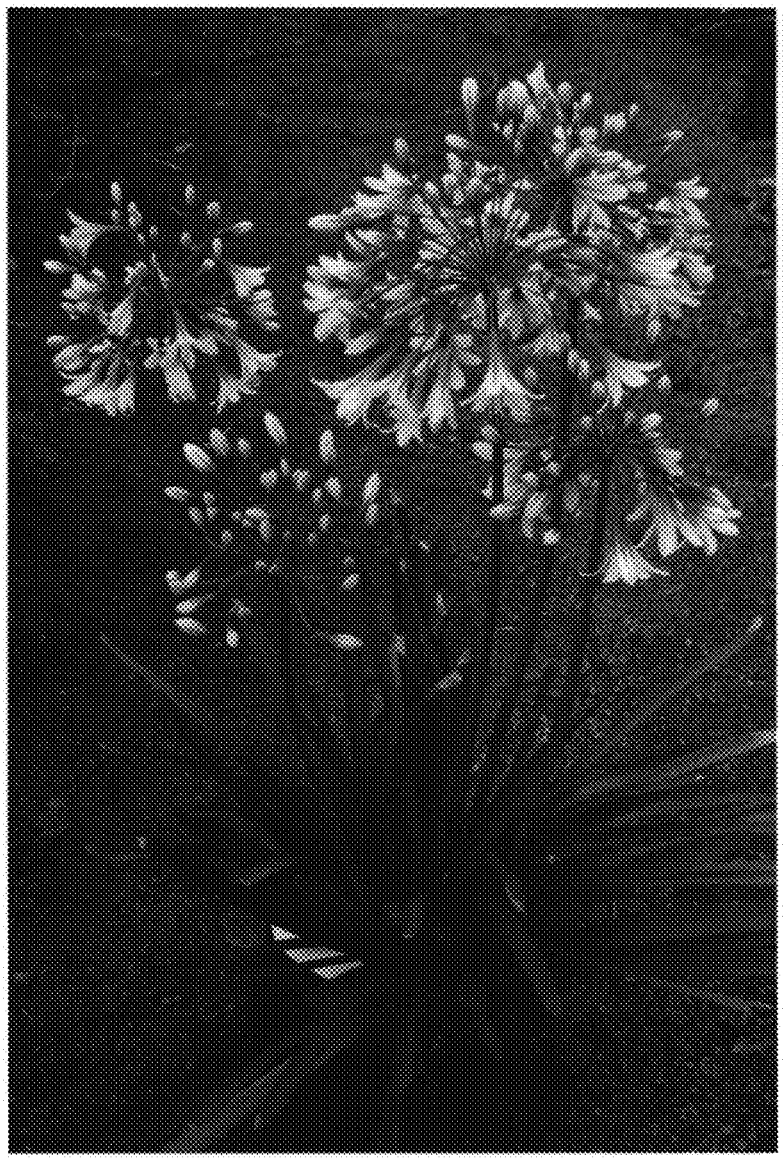
Figure 2:
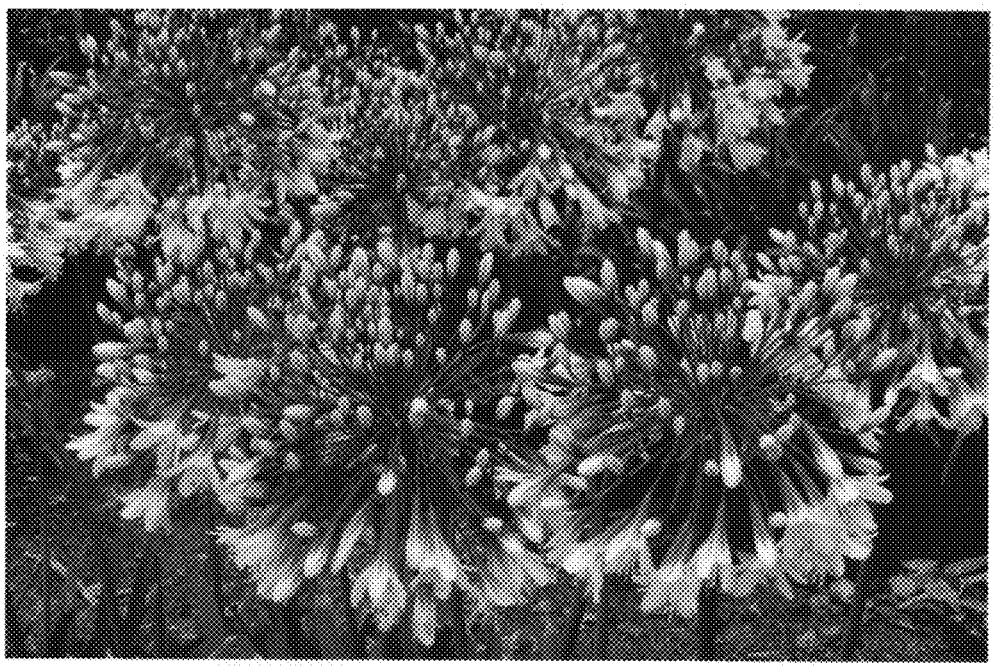

The photograph in FIG. 2 provides a close-up view of the inflorescences of 'MDB001'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 1 year-old plants (from a bare root division) of 'MDB001' as grown outdoors in 3-gallon containers in Loxley, Ala. The phenotype of the new cultivar may vary with variations in environmental, climatic, and cultural conditions, as it has not been tested under all possible environmental conditions. The color determinations are in accordance with The 2015 R.H.S.

Colour Chart of The Royal Horticultural Society, London, England, except where general color terms of ordinary dictionary significance are used.

General description:

*Blooming period*.—Blooms from early to mid summer in South Africa.

*Plant type*.—Semi-deciduous (climate dependent) herbaceous perennial.

*Plant habit*.—Medium statured with broad, short leaves emerging from basal rosettes with inflorescences emerging from the rosette centers.

*Height and spread*.—30 to 40 cm in height (foliage), 65 to 75 cm in height (including inflorescences) and an average of 45 cm in spread as a one year-old plant in a container.

*Cold hardiness*.—At least to U.S.D.A. Zone 8.

*Diseases*.—Good resistance has been observed to root and crown rot caused by *Fusarium* sp. and soft rot caused by *Erwinia* sp.

*Root description*.—Thick and fleshy, 161D in color.

*Propagation*.—Tissue culture (preferred) and division.

*Growth rate*.—Vigorous.

*Number of shoots* (*rosettes*).—An average of 10 as grown in a 3-gallon container.

Foliage description:

*Leaf shape*.—Ligulate.

*Leaf division*.—Simple.

*Leaf base*.—Truncate.

*Leaf arrangement*.—2-ranked, arranged in shoots an average of 4 cm in diameter at base.

*Leaf apex*.—Narrow acute.

*Leaf aspect*.—Emerging leaves erect, then cascade.

*Leaf venation*.—Parallel, upper surface; matches leaf coloration, and lower surface; with only mid rib on lower surface conspicuous; color 146D.

*Leaf margins*.—Entire.

*Leaf size*.—An average of 30 cm in length and 3.5 cm in width.

*Leaf surface*.—Smooth, glabrous, and dull on upper and lower surface.

*Leaf number*.—Average of 15 leaves per rosette.

*Leaf color*.—Young leaves, upper and lower surface; 144A and blending to 146B near apex and 145D to 145B at base, mature leaves upper surface; 138A suffused with 137A and 144A near base with very base 196D suffused with NN155D, mature leaves lower surface; 138A and 144A near base with very base 149D.

*Leaf attachment*.—Sessile to base.

Flower description:

*Inflorescence type*.—Dense umbel with pendulous flowers.

*Flower fragrance*.—Very light pleasant fragrance.

*Flower type*.—Rotate, campanulate, base of tepals fused.

*Flower number*.—An average of 90 flowers per umbel.

*Inflorescence size*.—Average of 15 cm in height (excluding peduncle) and 20 cm in diameter.

*Flower size*.—An average of 4.5 cm in depth and diameter.

*Flower type*.—Tubular-campanulate.

*Lastingness of inflorescence*.—About one month, flowers an average of 7 days.

*Flower aspect*.—Outward to drooping.

*Peduncle*.—Very strong, round in shape, held primarily upright, up to 60 cm in length and 1.2 cm in width at distal region and 1.8 cm in width at proximal region, a blend of N144C and N144D in color with base N144D and slightly suffused with 139D, satiny, glabrous and slightly glaucous surface.

*Pedicels*.—Moderately strong, average of 6 cm in length and 2 mm in width, held erect to outward (0° to 180°) and becoming pendulous as they mature, N144C in color, glabrous surface.

*Flower buds*.—Oblanceolate in shape, average of 4 cm in length and 1 cm in width at the widest point towards the tip, 5 mm in width at the narrowest point towards the base, color is a blend of NN155C and 157A and light hues of N144C at the very apex with lower half a color between 94B and 95C.

*Tepals*.—Average of 6, linear to oblanceolate in shape, rounded to acute apex, margins are translucent and entire, lower 20% of base is fused, inner and outer surfaces are glabrous and satiny, thick texture, average of 4 cm in length, 1 cm in width, inner and surface NN155C in color with a center vein that is translucent and 145D in color, tube portion is 1.5 cm in length and 7 mm in width, outer surface, bi-color with NN155C on upper portion and a color between 94B and 95C on lower portion with lines of a color between 94B and 95C extending into upper free portion.

Reproductive organs:

*Gynoecium*.—1 pistil, stigma is very minute, less than 0.5 mm in diameter and 157D in color, style is oval in shape, 3 cm in length, 1 mm in diameter and NN155C in color, surface is shiny and glabrous, ovary is superior, oblong in shape, 1.3 cm in length, 4 mm in width, N144B in color.

*Androecium*.—7 stamens, anthers are dorsifixed, oblong in shape, average of 3 mm in length, 1 mm in diameter, 147A in color, filament is 3 cm in length, 1 mm in diameter, round in shape, glabrous surface, NN155C in color, pollen is low in quantity and 14B in color.

*Fruit/seed*.—Have not been observed to date.

It is claimed:

1. A new and distinct cultivar of *Agapanthus* plant named 'MDB001' as herein illustrated and described.

* * * * *